United States Patent [19]

Day

[11] Patent Number: 4,545,572
[45] Date of Patent: Oct. 8, 1985

[54] APPARATUS FOR HOLDING THE HEAD OF A PATIENT FOR SURGERY

[75] Inventor: James L. Day, Cincinnati, Ohio

[73] Assignee: Ohio Medical Instrument Company, Inc., Cincinnati, Ohio

[21] Appl. No.: 642,634

[22] Filed: Aug. 20, 1984

[51] Int. Cl.[4] ............................................. A61G 13/00
[52] U.S. Cl. .................................................. 269/328
[58] Field of Search ................... 269/328, 45, 156; 128/346, 134; 5/434, 437; 297/403, 407–410

[56] References Cited

U.S. PATENT DOCUMENTS 2,452,816 11/1948 Wagner .
2,535,559 12/1950 Wolf .
2,966,383 12/1960 Boetcker et al. .
3,835,861 8/1974 Kees, Jr. et al. .
4,108,426 8/1978 Lindstroem et al. .
4,169,478 10/1979 Hickmann .
4,321,718 3/1982 Chern .

FOREIGN PATENT DOCUMENTS 478651 2/1953 Italy .

Primary Examiner—Robert C. Watson
Attorney, Agent, or Firm—Wood, Herron & Evans

[57] ABSTRACT

Apparatus for holding a patient's head for surgery thereon so that the head is accessible from ear to ear and from occiput to and including the orbits. The apparatus holds the head clamped between opposed clamp pads. Rear support means engages the posterior of the head and a pair of face pads are adjustably positionable just below the cheekbones of the patient and are lockable in such position. The face pads and rear support means are releasably movable toward one another to hold the head securely between them.

14 Claims, 3 Drawing Figures

4,545,572

APPARATUS FOR HOLDING THE HEAD OF A PATIENT FOR SURGERY

FIELD OF THE INVENTION

This invention relates to a device for holding the head of a patient, especially a younger child or infant, during surgery in which the head from ear to ear and from occiput to and including the orbits must be accessible for the surgical procedure.

PRIOR ART

Hickmann U.S. Pat. No. 4,169,478 shows a "crown of thorns" head clamp wherein the skull is held rigidly between three skin-piercing pins, mounted on opposite sides of a bracket, which engage the back and front of the head. Keys and Hickmann U.S. Pat. No. 3,835,861 is similar. Lindstroem et al U.S. Pat. No. 4,108,426 shows a surgical device wherein the head is engaged by a pin in the front and against two pressure pads in the posterior portion. Wagner U.S. Pat. No. 2,452,816 shows a jaw supporting appliance having a pair of jaw pads mounted on arms which hold the jaw in closed position when the patient is anesthetized in recumbent position during a surgical procedure. Italian Pat. No. 478,651 also shows a device having a pair of opposed pads for engaging the head.

BACKGROUND OF THE INVENTION

As is apparent from the foregoing prior art, it has been the practice in skull surgery to immobilize the head of a patient by positioning one or more pins into the skull to immobilize the head, typically in a three point grip at the back and at the front of the forehead. However, the use of a "crown of thorns" type head clamp is not suitable in all circumstances, especially where the patient is a child or infant whose bone structure has not hardened or where extreme pressure at a pin tip could pierce bone structure or collapse the skull. Also, in some surgical procedures where the front of the forehead must be accessible in order to correct bone malstructure, a pin or other gripping means at this position would obstruct the surgeon's field.

The apparatus of this invention is a clamp whereby the head is held by non-piercing pressure exerted on the cheekbones rather than on the forehead. The skin is not pierced but rather is gripped by external, pressure-exerting clamp pads placed below and just adjacent the cheekbones, and at the back of the head.

BRIEF SUMMARY OF THE INVENTION

The present invention contemplates a method of immobilizing a patient's head, in either a supine or an upright position, for surgery on the skull and orbits, wherein the posterior portion of the head is seated against a rear support means, two face pads are swung into position adjacent each cheekbone of the patient, and locked in such position, and the rear support means is moved relatively toward the face pads to exert pressure on the head sufficient to hold it immobile between the rear support means and the face pads, while leaving unobstructed the entire top of the head and the orbits.

Apparatus in accordance with the invention comprises a bracket to which a pair of arms are connected by universal joints. Locking means are provided to lock each arm in desired orientation with respect to the bracket. Each arm has a face pad adjustably mounted to it for engagement against a cheekbone of the patient. Rear support means are mounted by the bracket for engaging the posterior of the head. The face pads can be oriented to project generally toward the rear support means. The rear support means can be advanced toward the face pads when the latter are locked in place against the cheekbones, to hold a head immobile between the face pads and the rear support means.

In the preferred form of the invention the bracket is generally C-shaped and the arms project from the ends of the bracket, with the face pads pivotally mounted at the respective ends of the arms.

DESCRIPTION OF THE DRAWINGS

The invention can best be further described and explained by reference to the accompanying drawings, in which.

DETAILED DESCRIPTION

Figure 1:
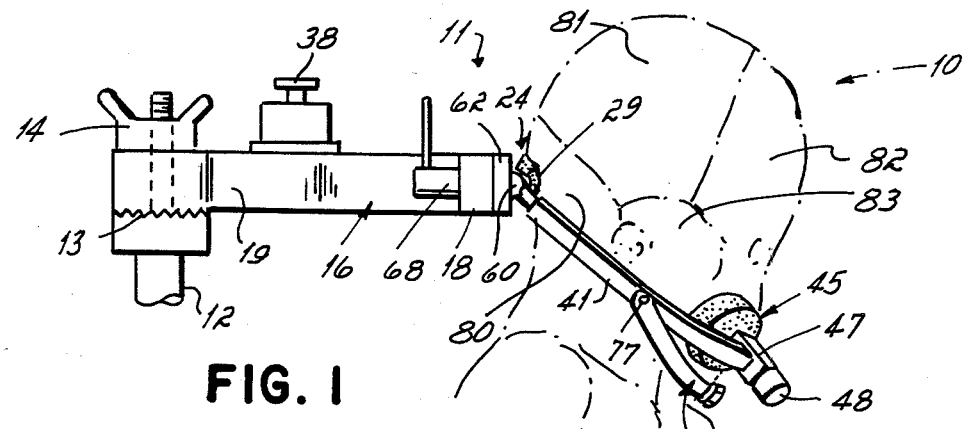
FIG. 1 is an elevation partially broken away, showing a preferred form of the apparatus of this invention in use to hold the head of a patient upright for operation on the upper part of the skull and orbits.

The apparatus 11 of this invention can be used to hold the head of a patient 10 upright, as shown in FIG. 1, or alternatively in a supine position. The latter position is often used for infant patients. For purposes of description, the apparatus is described hereinafter with reference to the upright patient orientation of FIG. 1.

The apparatus 11 holds the head of the patient 10 so that the upper portion of the skull and orbits is accessible and unobstructed for surgery. The apparatus may be mounted from a standard or support 12, as by interlocking teeth 13 which are held in engagement by a screw 14.

Figure 2:
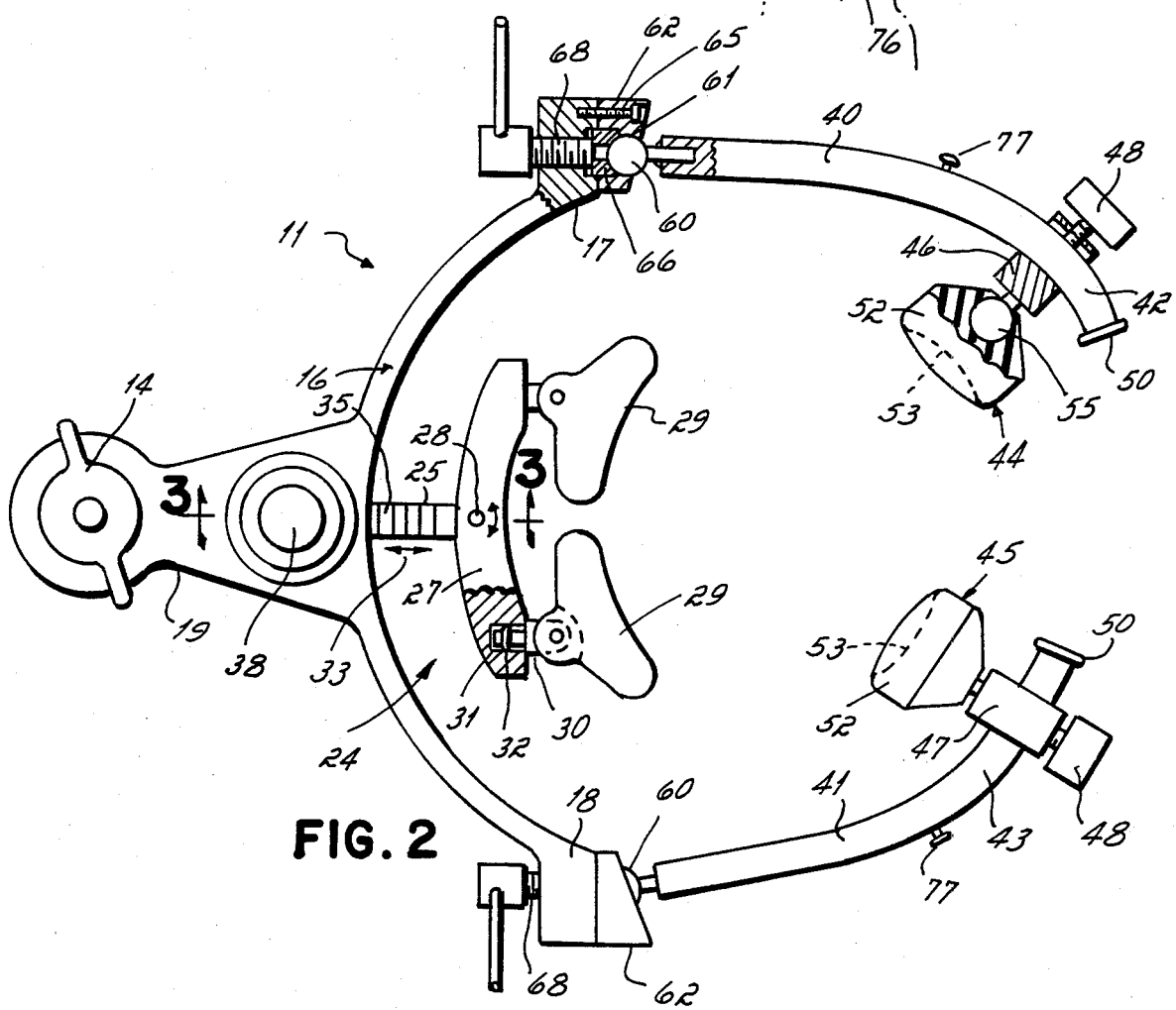
FIG. 2 is an enlarged top plan view, partly broken away, of a preferred form of the apparatus.

As best shown in FIG. 2, the apparatus includes bracket 16 which is preferably substantially C-shaped or semicircular, and which has opposed extremities or ends 17, 18. The bracket has a rearward extension 19 on which the mounting teeth 13 are provided.

A head posterior or rear support means designated generally at 24, is mounted by bracket 16, preferably at the middle thereof and in line with the axis of extension 19. The rear support means 24 includes a slidably adjustable mounting leg 25 and a base 27 which is pivotally mounted at its center to leg 25, as at 28. As indicated by the arrow, base 27 can pivot about leg 25 in the plane of the bracket. The base itself is preferably curved similarly to the curvature of the bracket, and at its ends is provided with a pair of tiltable posterior support pads 29, 29. The support pads comprise cushioned members pivotally carried on mounts 30, and are removably seated in blind sockets 31 in the respective ends of the base 27. One such mount and socket is shown in section in FIG. 2, the other being similar. An O-ring 32 may be provided in a groove on the mount 30 to provide a releasable frictional interfit with socket 31 for easy removal of the support pad, for example for cleaning or sterilization.

Figure 3:
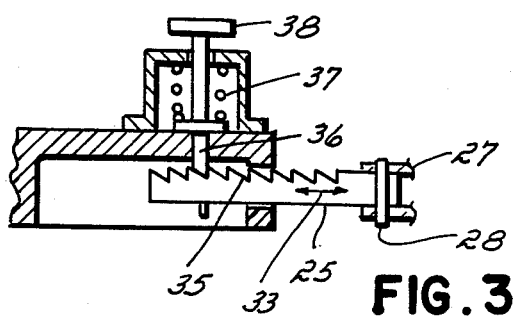
FIG. 3 is a vertical section taken on line 3—3 of FIG. 2.

The two support pads 29, 29 are configured and positioned to provide support for the posterior of the head and in use engage the occipital area of skull, as shown in FIG. 1. The rear support means 24 is adjustably movable toward and away from bracket 16, as indicated by the arrow 33 in FIG. 2. For this purpose leg 25 is provided with ratchet teeth 35 (see FIG. 3) which are engagable by a pawl 36. The pawl is biased by a spring 37 toward engagement with the teeth 35. Teeth 35 are oriented so that the rear support means 24 can be pushed away from bracket (toward the head) 16 but not toward the bracket. The purpose of this, as will be shown, is to enable clamping force to be applied at the rear of the head after the face pads have first been positioned. In order to release the head from the apparatus, pawl 36 is released by a pull 38, which permits the rear support means to be moved away from the head and back toward the bracket 16.

At the ends 17, 18 of bracket 16, there are pivotally, preferably universally, mounted arms 40 and 41, respectively. These arms are desirably curved inwardly at the outer portions, as at 42, 43, respectively, as viewed in plan in FIG. 2. In use the arms and the bracket form an approximately oval or circular form. The arms may be formed from square-sectioned rod. Face pads, generally designated by 44, 45, are adjustably mounted to the respective arms for movement along the curved portion 42, 43. In the embodiment shown, the face pads 44, 45 comprise sliders 46, 47, each having an aperture through which the curved arm portion 42, 43 passes. Screw means 48 are provided to lock the respective face pads 44, 45 at desired position along the arms. The sliders are captured on the arms by end stops 50, 50 secured to the ends of the arm, sized larger than the apertures in the sliders 46, 47. Each face pad includes a foam or cushion member 52 presenting a concave pocket 53 configured to be engaged just under the cheekbone on the face of the patient. The cushion members 52, 52 are snapped on over ball mounts 55 on the sliders (one of which is shown in section in FIG. 2).

As mentioned, the arms 40, 41 are universally connected to bracket 16, preferably at the ends thereof. One of these universal mounts is shown in FIG. 2, the other being similar. A ball 60 is secured as by brazing at the inner end of the respective arm. Ball 60 is seated in a socket 61 in a cap 62, which is secured by bolts, one of which is shown at 65, to a boss at the end of bracket 16. A washer 66 is seated in an aperture formed between the cap 62 and the bracket end, and this washer can be tightened against ball 60 by a screw 68 to lock the ball in its socket 61, thereby to fix the orientation of the arm with respect to bracket 16.

In use, the arms project at about a 30 degree angle from the plane of bracket 16. The arms 40, 41 are movable by their connection to the bracket to permit the face pads 44, 45 to be aligned and brought into engagement under the cheekbones, see FIG. 1.

The patient is positioned with the posterior of the head resting against the posterior support pads 29, 29. The arms are adjusted with respect to the bracket by the universal joints, and the face pads 44, 45 can be adjusted along the length of the arms so that the pads are brought into position just below the cheekbones. With the arms and the face pads tightened in locking position, the rear support means 24 is then pressed forwardly from the bracket, as by thumb pressure. The ratchet 35 holds the base in such position until released. In this manner the head is both immobilized and held upright as shown in FIG. 1, without need for pins or piercing the skin. It will be noted that the pads, directed upwardly and rearwardly toward the rear support exert some lifting force and hold the head upright to prevent it from slipping downwardly. As a further precaution, a chin strap 76 (see FIG. 1) can be attached beneath the jaw to provide further upright support. The strap can be secured from buttons or snaps 77, 77 on the arms 40, 41.

For reference, the occipital, parietal, frontal, and temporal regions of the head are approximated by dotted lines shown in FIG. 1, and are designated respectively by 80, 81, 82, and 83.

Having described the invention, what is claimed is:

1. Apparatus for holding a patient's head for surgery on the top of the skull and orbits, comprising
   a bracket,
   rear support means mounted by said bracket for engaging the posterior of the patient's head,
   a pair of arms,
   means universally connecting each arm to said bracket at spaced positions thereon so that the arms are independently movable with respect to the bracket,
   means for locking each universal connecting means to lock each arm in desired orientation with respect to said bracket,
   each arm having a face pad adjustably mounted to it for engagement just below a cheekbone of said patient, said face pads facing toward said rear support means,
   said face pads being positionable adjacent the cheekbones to hold the head securely against the rear support means.

2. The apparatus of claim 1 wherein said arms are mounted at ends of said bracket and in use extend from it along each side of the patient's head, and said rear support means is mounted to the bracket, between the arms.

3. Apparatus for holding a patient's head for surgery on the top of the skull and orbits, comprising
   a bracket,
   rear support means mounted by said bracket for engaging the posterior of the patient's head,
   a pair of arms universally connected to said bracket at spaced positions thereon, said arms mounted at ends of said bracket and in use extending from it along each side of the patient's head,
   said rear support means mounted to the bracket between the arms,
   means for locking each arm in desired orientation with respect to said bracket,
   each arm having a face pad adjustably mounted to it for engagement just below a cheekbone of said patient, said face pads facing toward said rear support means,
   said face pads being positionable adjacent the cheekbones to hold the head securely against the rear support means,
   said arms and bracket configured to define a generally oval shape, said rear support means and the face pads projecting into the oval.

4. The apparatus of claim 3 wherein said rear support means is mounted by a leg which projects toward the center of said oval, from said bracket.

5. The apparatus of claim 4 wherein said rear support means comprises a base mounted to said leg and having two head rests pivotally mounted to it.

6. The apparatus of claim 5 wherein said leg includes ratchet means whereby it can be moved away from said bracket and into said oval, but resists movement in the reverse direction toward the bracket.

7. Apparatus for holding a patient's head for surgery on the top of the skull and orbits, comprising a bracket, rear support means mounted by said bracket for engaging the posterior of the patient's head, a pair of arms universally connected to said bracket at spaced positions thereon, means for locking each arm in desired orientation with respect to said bracket, each arm having a face pad adjustably mounted to it for engagement just below a cheekbone of said patient, said face pads facing toward said rear support means, said face pads being positionable adjacent the cheekbones to hold the head securely against the rear support means, said arms being curved toward said bracket and said face pads positioned near the ends of the arms, so as to face said rear support means.

8. The apparatus of claim 7 wherein said face pads are slidable on said arms for movement therealong.

9. The apparatus of claim 7 wherein said bracket is C-shaped.

10. The apparatus of claim 1 wherein each arm is connected to said bracket by universal connecting means comprising a ball and a socket in which the respective ball is received.

11. Apparatus for holding a patient's head for surgery on the top of the skull and orbits, comprising a bracket, rear support means mounted by said bracket for engaging the posterior of the patient's head, a pair of arms universally connected to said bracket at spaced positions thereon, each arm being connected to said bracket by universal connecting means comprising a ball and a socket in which the respective ball is received, means for locking each arm in desired orientation with respect to said bracket, the arm locking means comprising screw means for pressing said ball frictionally into said socket, each arm having a face pad adjustably mounted to it for engagement just below a cheekbone of said patient, said face pads facing toward said rear support means, said face pads being positionable adjacent the cheekbones to hold the head securely against the rear support means.

12. Apparatus for holding a patient's head for surgery on the top of the skull and orbits, comprising a bracket, rear support means mounted by said bracket for engaging the posterior of the patient's head, a pair of arms universally connected to said bracket at spaced positions thereon, means for locking each arm in desired orientation with respect to said bracket, each arm having a face pad adjustably mounted to it for engagement just below a cheekbone of said patient, said face pads facing toward said rear support means, said face pads being positionable adjacent the cheekbones to hold the head securely against the rear support means, and mounting means projecting from said bracket, for mounting the apparatus to a standard.

13. Apparatus for holding a patient's head for surgery on the top of the skull and orbits, comprising a bracket, rear support means mounted by said bracket for engaging the posterior of the patient's head, a pair of arms universally connected to said bracket at spaced positions thereon, means for locking each arm in desired orientation with respect to said bracket, each arm having a face pad adjustably mounted to it for engagement just below a cheekbone of said patient, said face pads facing toward said rear support means, said face pads being positionable adjacent the cheekbones to hold the head securely against the rear support means, and chin strap means mounted from said apparatus and engageable beneath the chin of the patient to hold the chin upwardly toward said rear support means and face pads.

14. Apparatus for holding a patient's head for surgery on the top of the skull and orbits, comprising a bracket, rear support means mounted by said bracket for engaging the posterior of the patient's head, a pair of face pads supported from said bracket and adjustably positionable for engagement just below the cheekbones of said patient, said face pads facing toward said rear support means, means for locking the face pads in fixed position with respect to the bracket, said face pads and rear support means being movable toward one another to clamp the head securely between them, said face pads being concave and positioned below the rear support means with respect to said bracket, to engage the head just under the cheekbones thereof.

* * * * *